United States Patent [19]

Breillatt, Jr. et al.

[11] Patent Number: 5,276,146

[45] Date of Patent: Jan. 4, 1994

[54] LIQUID PERFLUOROCARBON SUPPORTS USEFUL AS LIQUID AFFINITY SUPPORTS

[75] Inventors: Julian P. Breillatt, Jr., Mundelein, Ill.; John W. d. Eveleigh, Hockessin, Del.

[73] Assignee: E. I. Du Pont de Nemours and Company, Wilmington, Del.

[21] Appl. No.: 761,152

[22] Filed: Sep. 17, 1991

Related U.S. Application Data

[63] Continuation of Ser. No. 134,026, Dec. 17, 1987, abandoned, which is a continuation-in-part of Ser. No. 32,642, Mar. 31, 1987, abandoned, which is a continuation-in-part of Ser. No. 863,607, May 15, 1986, abandoned.

[51] Int. Cl.$^5$ .................. A23J 1/00; C07K 3/00; B01D 15/08; C02F 1/28
[52] U.S. Cl. .................. 530/413; 530/412; 210/635; 435/6; 436/518; 436/528; 264/4.1; 428/402.2
[58] Field of Search .................. 435/6; 530/412, 413; 210/635; 436/518, 528; 264/4.1; 428/402.2

[56] References Cited

U.S. PATENT DOCUMENTS

| 4,101,380 | 7/1978 | Rubinstein et al. | 195/63 |
| 4,299,916 | 11/1981 | Litman et al. | 435/6 |
| 4,619,904 | 10/1986 | Giaver et al. | 436/518 |
| 4,634,681 | 1/1987 | Giaver et al. | 436/518 |

OTHER PUBLICATIONS

Keese et al. Proc Natl Acad Sci 80: 5622-26 (1983).
Lehninger, Biochemistry (1970) Worth Publishers, N.Y., N.Y. pp. 150-165.
Merck Index 10th Edition (1983) p. 8312.
Rawn, Biochemistry Harper & Row (1983) pp. 767-781.
Munns et al. Prog Nucl Acids Res (1980) pp. 109-165.

Primary Examiner—Margaret Moskowitz
Assistant Examiner—Scott A. Chambers

[57] ABSTRACT

Liquid perfluorocarbon supports useful as liquid affinity supports are provided. The support is based on an inert perfluorocarbon carrier with ligands or binders for the ligands attached to its surface through a highly fluorinated isocyanate anchor group.

8 Claims, No Drawings

LIQUID PERFLUOROCARBON SUPPORTS USEFUL AS LIQUID AFFINITY SUPPORTS

CROSS REFERENCE TO RELATED APPLICATION

This is a continuation of application Ser. No. 07/134,026, filed Dec. 17, 1987, abandoned which is a continuation-in-part of an application entitled Bioaffinity Separations with Liquid Affinity Supports, Ser. No. 07/032,642, filed Mar. 31, 1987 now abandoned, which is a continuation-in-part of Ser. No. 06/863,607, filed May 15, 1986 now abandoned, both by Julian P. Breillatt, Jr. et al.

TECHNICAL FIELD

This invention is related to the performance of affinity and ion exchange separations and more specifically to the performance of bioaffinity and ion exchange separations utilizing perfluorocarbon fluid-based liquid supports and their use in capturing molecules through specific binding and ionic reactions.

BACKGROUND ART

An affinity separation can be defined as any separation achieved by employing the specific binding of one molecule by another. Bioaffinity separation is defined as an affinity separation in which one of the components involved in the affinity reaction is biologically active or is of biological interest. Bioaffinity separations generally involve at least one biomacromolecule, such as a protein or nucleic acid, as one of the components of the binding pair. Examples of such bioaffinity binding pairs include: antigen-antibody, substrate-enzyme, effector-enzyme, inhibitor-enzyme, complementary nucleic acid strands, binding protein-vitamin, binding protein-nucleic acid; reactive dye-protein, reactive dye-nucleic acid; and others; the terms ligand and binder will be used to represent the two components in specific bioaffinity binding pairs. This type of specific binding is distinct from the partitioning of a solute between two solvents. Such partitioning is based on hydrophilicity or hydrophobicity considerations and is relied on, for example, in solvent extraction, high performance liquid chromatography and gas liquid chromatography.

Affinity separations are generally considered to require the use of solid supports derivatized with a ligand or binder. These separations can be configured as batch processes or chromatographic processes with the latter generally being preferred. Affinity chromatography is well known and has been reviewed, for example, in C. R. Lowe, "An Introduction to Affinity Chromatography", North Holland Publishing Company, Amsterdam, N.Y. 1978. Lowe describes the characteristics desirable in a solid support to be used in an affinity separation. According to Lowe, the solid support should form a loose, porous network to allow uniform and unimpaired entry and exit of large molecules and to provide a large surface area for immobilization of the ligand; it should be chemically inert and physically and chemically stable; and the support must be capable of functionalization to allow subsequent stable coupling of the ligand. Additionally, the particles should be uniform, spherical and rigid to ensure good fluid flow characteristics.

The list of support materials suitable for affinity chromatography is extensive and will not be reviewed here (see Lowe, 1978, for a partial listing). It is not generally possible for a given support to achieve all of the above objectives. One compromise is evident in the use of high surface area porous supports, such as porous glass or porous polyacrylamide beads. These type supports have the disadvantage that washing away contaminating substances is difficult due to the tortuous paths and dead end channels in these supports [Eveleigh, Journal of Chromatography, Volume 159, 129-145 (1978)]. Another disadvantage of porous supports is that not all of the surface area is usable with large macromolecules. That is, the pore size may be too small to allow the macromolecule to enter thereby limiting the effective surface area and capacity [Zaborsky, Biomedical Applications of Immobilized Enzymes and Proteins, Volume 1, p. 41, Ed. Chang, Plenum Press (1977)].

A further practical disadvantage of standard solid support affinity chromatography is the decreasing efficiency of the column as binding sites at the incoming end of the column become filled with the target binder molecules. The binder then must flow further down the column to find a free ligand and, therefore, the probability of the elution of the target prior to binding increases. Countercurrent chromatography where the sample is constantly exposed to fresh support overcomes this disadvantage. However, affinity supports are not generally amenable to such processes because the support is not conveniently pumped as a slurry. Solid supports are ideally suited for use in packed beds (e.g., columns): they can be packed well, are easily retained on porous frits and, being rigid, are self supporting. Problems arise, however, when one tries to transport them. They tend to sediment irreversibly in low flow areas, pack together as a mass if obstructed, and the particles abrade by contact with each other and the containing walls. Slurries of particles could be transported at low concentrations. That, however, is impractical requiring transportation of the carrier fluids also. A major problem in designing a practical continuous system is how to transport a packed slurry without carrying over fluids from one stage to the next. Seals or gates introduce abrasion and invariably leak or fail by virtue of compaction of sediment within them and fragmentation of the support rapidly becomes apparent.

Continuous chromatographic separation, using solid supports, has been made possible using a rotating annular bed in which sample is applied at a fixed point in a descending curtain of elution fluid, separated components being collected around the lower periphery. Such devices are cumbersome to construct and operate and suffer from the major disadvantage that the bulk of the bed (support) is not being utilized for the separation, Furthermore, problems associated with an even distribution of eluant flow, sealing, and optimization of the separation have inhibited general exceptance of the approach.

A still further disadvantage of solid supports is their propensity to become plugged with debris from the sample. This may be cellular debris from a biological sample or physical debris from other sources, but samples frequently require filtration prior to processing in order to preserve the good flow characteristics of the column.

Affinity separations often form a component part of other processes. One example is their use in heterogeneous immunoassays. Here the affinity separation is used to capture an analyte from a complex mixture such as serum or plasma. After capturing the analyte, the contaminants are washed away and the analyte is detected using any number of well known assay protocols.

Some common solid supports in this area are plastic spheres (beads), interiors of plastic test tubes, interiors of microtitre plate wells, magnetic particles, and porous glass particles. The largest disadvantage of these systems is the generally limited surface area which limits capacity and capture efficiency. This, in turn, leads to a limitation in sensitivity (change in response/change in concentration) and detection limit (minimum detectable concentration).

Certain separation problems have been traditionally dealt with by liquid-liquid extractions. For example, in nucleic acid hybridization assays, requiring purified nucleic acid, a nucleic acid from the sample, such as DNA or RNA, needs to be bound to a solid support. To obtain the nucleic acid to be probed it must first be released from a cell (if within a cell), by lysis, then extracted from the lysate. The most common extraction technique uses an aqueous phenol/chloroform mixture (Maniatis et al., Molecular Cloning: A Laboratory Manual, pp. 458-9, Cold Spring Harbor Laboratory, 1982). Proteins, which are the major component of the lysate, tend to interfere with the extraction. Following extraction of the nucleic acid, excess phenol must be extracted with ether and then the ether evaporated. The nucleic acid containing solution is then concentrated prior to deposition on a solid support; see, for example, Church et al, Proc. Nat. Acad. Sci. USA, Volume 81, 1991 (1984). This is a tedious and hazardous process with many opportunities for material losses along the way.

Some liquid phase affinity partitioning separations have been achieved. P-A Albertsson, "Partition of Cell Particles and Macromolecules", Almquist and Wiksell, Ed.; Wiley, New York, 1971, reported the development of a partitioning system based on the immiscibility of aqueous solutions of dextran and polyethylene glycol. S. D. Flanagan et al., Croatian Chem. Acta, Volume 47, 449 (1975), adapted that system to allow affinity mediated separations by attaching ligands to the polyethylene glycol thus allowing specific binding affinities to drive the separation. This system has limited utility in that it requires that the binder first partition into the phase containing the ligand to some degree before the specific binding interaction can occur. The system is further limited in that it is applicable only to batch processes and not to chromatographic processes.

Perfluorocarbon emulsions have been used to study cell-substrate interactions as reported by Keese et al. [Proc. Nat. Acad. Sci. USA, Volume 80, 5622-5626 (1983)]. While anchorage-dependent cells are traditionally grown on solid supports, Keese et al. have shown that they can be grown at the phase boundary between liquid perfluorocarbons and tissue culture medium. Keese et al. showed that surface active compounds such as pentafluorobenzoyl chloride provided an effective surface for growing such cells. However, because of evidence indicating no reaction between the acid halide and the cells or proteins present in the culture medium, the authors speculated that the pentafluorobenzoyl chloride was hydrolyzed to form pentafluorobenzoic acid on the surface of the perfluorocarbon droplet. The authors further speculated that the acid surface caused a layer of denatured protein to deposit on the surface of the liquid perfluorocarbon providing a suitable surface for attachment of the cells. As further proof of the lack of acid chloride-amino group reactions, the authors obtained cell attachment and proliferation by sonicating the emulsion, without perfluorobenzoyl chloride, with water or ethylene glycol. Keese et al. speculated that unknown surface active compounds were being formed by this treatment.

Because affinity separation is a powerful technique and because currently available supports suffer from various disadvantages, there is a need for improved supports. These should have the following properties: physical and chemical stability; chemical inertness; compatibility with a variety of biological samples; utility in batch and chromatographic applications and in countercurrent type applications; high surface area; ability to allow high flow rates in chromatographic applications; ability to provide for ready and stable attachment of ligands or binders to the surface; allow simple concentration of the captured product; allow easy automation of any separation process; and allow simple efficient regeneration of the support.

DISCLOSURE OF THE INVENTION

The liquid supports of this invention are based on liquid perfluorocarbon carriers to which ligands or binders are securely attached through a highly fluorinated isocyanate anchor group. The liquid supports are chemically inert, immiscible with water, have specific gravity significantly different from water, and have low nonspecific binding to the ligands and binders.

The method of conducting bioaffinity separations comprising the steps of:
1) forming a liquid support by attaching a ligand or binder to the surface of the droplets of an emulsion of a liquid perfluorocarbon carrier through a highly fluorinated isocyanate anchor group; and
2) capturing a target binder or ligand, complementary to the ligand or binder attached to the carrier from a mixture using said liquid support.

The ligand or binder is attached to the surface through modification of the surface or of the ligand or binder by the direct or the partition method utilizing a highly fluorinated isocyanate anchor group based on a compound having the formula:

$R_F$—CH$_2$CH$_2$CH$_2$—NCO wherein $R_F$ is linear, branched, or cyclic perfluorinated radical from 1 to 20 carbon atoms.

DISCUSSION OF THE INVENTION

The liquid supports of this invention offer unprecedented advantages in carrying out bioaffinity separations. Since the liquid supports of this invention, in addition to being liquid affinity supports also include such separations which rely on charged interactions, e.g. when the ligand attached to ths carrier is a charged organic moiety and the separation of the desired product from its environment is by the process commonly referred to as ion exchange separation (chromatography), the bioaffinity separations of this invention are intended to include such ion exchange separations and the liquid affinity supports are intended to include liquid ion-exchange supports. Two of the greatest advantages of using a liquid affinity support are: allowing development of countercurrent affinity separations and allowing simple concentration of the captured product. Other advantages are allowing easy automation of the separation process and allowing high flow rates in chromatographic applications. The liquid supports of this invention offer additional properties such as being stable in an aqueous environment; being immiscible with water; having a specific gravity significantly different from water, preferably heavier, allowing easy separation from the aqueous environment; having low nonspecific binding to native proteins, nucleic acids or other components of biological samples; and being incapable of dissolving any extraneous solutes present in a biological sample.

The liquid affinity supports of this invention comprise a carrier and ligands or binders which are securely attached through a highly fluorinated isocyanate anchor. Carriers useful in carrying out bioaffinity separations have the properties described above and include liquid perfluorocarbons (LPF), hydrocarbons, and silicones. By perfluorocarbon is meant a molecule which contains the largest possible or a relatively large proportion of fluorine atoms in its structure.

LPF's are known to be inert and biocompatible. Liquid perfluorocarbons have been used as blood substitutes in the form of emulsions of perfluorocarbons in isotonic buffers containing antibiotics [Agarwal, Defense Science Journal, Volume 30, 51-54 (1980)]. This use depends on the high solubility of oxygen in these emulsions and does not require any surface modification of the perfluorocarbon droplets. It does, however, require the presence of surfactants such as phospholipids to stabilize the emulsion. LPF's are immiscible with water and are very poor solvents for both hydrophilic and hydrophobic solutes. As a class, LPF's are dense liquids with specific gravities (approximately 2) allowing simple gravity separation of the support from the sample matrix.

Hydrocarbons and silicones are other classes of materials which meet the requirements to function as carriers in liquid affinity supports.

By ligand is meant an antigen, hapten, nucleic acid, enzyme substrate, vitamin, dye, charged organic molecules or other small organic molecule including enzyme effectors and inhibitors and by binder is meant an antibody, enzyme, nucleic acid, binding protein, synthetic mimics of binding proteins such as polylysine and polyethyleneimines or other biomacromolecule capable of specific binding or ionic (charged) interactions.

The highly fluorinated isocyanate anchor group is based on a compound having the formula $R_FCH_2CH_2CH_2NCO$, wherein $R_F$ is linear, branched, or cyclic perfluorinated radical from 1 to 20 carbon atoms. In a preferred class of the above compounds $R_F$ is a linear $F(CF_2)_n$ radical. A more specifically preferred compound is $F(CF_2)_8CH_2CH_2CH_2NCO$. These compounds can be made in the following manner. A starting fluorinated olefin, $R_F-CH=CH_2$, is contacted with HCN in the presence of a nickel catalyst and a Lewis acid promoter such as zinc chloride by a process similar to that disclosed in Drinkard et al., U.S. Pat. No. 3,496,217. By using conventional chemistry, the resulting nitrile, $R_F-CH_2CH_2-CN$, is converted to the amine, $R_F-CH_2CH_2CH_2-NH_2$, by a reaction with hydrogen in the presence of ammonia and Raney cobalt. The isocyanate, $R_F-CH_2CH_2CH_2-N=C=O$, then can be prepared by the reaction of the amine with phosgene.

The affinity support must have the ligand or binder securely attached to the carrier. By secure attachment is meant an attachment capable of surviving the steps involved in the bioaffinity and ion exchange separations while permitting two-dimensional mobility of the ligand on the carrier surface. However, it is expected that this attachment needs to be reversible when desired, for example, during the concentration step leading to a ligand-binder conjugate, such as by evaporation, and when desiring to regenerate the carrier, such as by competitive displacement of ligand or binder by perfluoro-surfactants. This is necessary so that ligand or binder does not contaminate the purified product and also to prevent loss of capacity of the support. With solid supports this is usually accomplished by covalently attaching the ligand or binder to the support. In addition to attaching securely ligand or binder, it is desirable not to alter the general inertness of the carrier nor introduce functional groups which might increase nonspecific binding. Further, it is desirable to develop general methods which will be applicable to a variety of ligands or binders.

One method for attaching ligands or binders to the surface of the carrier droplets to prepare a liquid affinity support is referred to as the direct method. In this method, an LPF containing a soluble reactive perfluorinated compound is emulsified with an aqueous solution of the ligand or binder. Compounds which are soluble in the LPF are generally those containing a high proportion of fluorine atoms. Commercially available perfluoroalkyl and perfluoroaryl compounds can be used. Suitable reactive groups are well known to those skilled in affinity chromatography; those reactive with amino groups being preferred. Examples of appropriate anchor compounds include pentafluorobenzoyl chloride, perfluorooctanoyl chloride, and perfluorooctanoyl anhydride, and perfluorooctylpropyl isocyanate. This isocyanate is a member of a class of compounds represented by the formula $R_F(CH_2)_3NCO$, wherein $R_F$ is as defined above. These compounds are described in applicants' assignee's copending application Ser. No. 07/134,027, filed on even date herewith, incorporated hereby by reference. The desired ligand or binder in aqueous solution is then emulsified with the carrier containing the reactive compound to permit the reaction of the reactive group with amino groups (or other suitable functional groups) on the ligand or binder.

It has been found that the amount of perfluorinated reagent on the surface of the droplet is important in obtaining an optimal layer of ligand or binder, for example, a protein. Too much reagent causes the deposition of very thick protein layers resulting in distorted and shear sensitive droplets. Further, thick coatings result in inefficient usage of the ligand or binder. Too little reagent results in low capacity supports which are also not desirable. The optimization of the amount of perfluorinated reactive reagent in this application is analogous to optimization of coupling reagents commonly used with solid supports and is well known to those skilled in preparing solid affinity supports. Among factors which are important in this process are the susceptibility of the reactive reagent to hydrolysis, the pH of the reaction mixture and the time of exposure.

The second and preferred method for preparing liquid affinity supports is referred to as the partition method. The basic difference between this and the direct method is that in the partition method the ligand or binder is modified to permit its selective high affinity (secure) binding to the surface of the carrier droplets. One means to accomplish this is to prepare and purify reagents, which contain a highly or perfluoro-substituted ligand or binder, prior to attachment to the surface. Several well known chemical strategies can be used to attach covalently highly fluorinated groups to ligands or binders. Factors which should be considered are reactivity of the fluorinated compound used, the pH of the reaction medium, the time and temperature of the reaction.

Compounds such as isocyanates, acid chlorides, anhydrides and imidazolides of various perfluorocarbon acids, for example, perfluorooctyl-propyl isocyanate, perfluorooctanoyl chloride, perfluorooctyl acetyl and propanoyl chlorides and perfluorooctanoyl and perfluorooctyl propanoyl imidazolides have been used successfully during the preparation of liquid affinity supports of this invention. The imidazolide derivative is preferred due to its lower reactivity allowing more controllable reactions. The most preferred class of compounds is the highly fluorinated isocyanates, as described above, an example being perfluorooctylpropyl isocyanate. The isocyanates are most preferred because of their increased stability to hydrolysis at the slightly alkaline reaction conditions generally used during the preparation of the liquid supports of this invention. In addition, the small amount of hydrolysis products formed (amines and ureas) do not interfere with the adsorption of the perfluoro-modified ligand or binder to the surface of LPF droplets when the partition method is used to form the liquid supports of this invention. This eliminates the need to purify the perfluoro-modified ligand or binder from the perfluoro-modification reaction milieu prior to forming the liquid support.

In general, the reactions are carried out by mixing an aqueous solution of the ligand or binder with the fluorinated reagent dissolved in a water miscible organic solvent such as tetrahydrofuran under controlled time, temperature and pH conditions. The derivatized ligand or binder can be separated from the by-products of the reaction and the organic solvent by gel filtration or dialysis. The degree of derivatization can be determined by any of the known techniques such as trinitrobenzene sulfonate labeling. The substituted ligand or binder is now ready to be used to form the liquid affinity support with an appropriate carrier such as a specific LPF. The liquid affinity support is formed by emulsifying the LPF such as perfluorodecalin with a buffered solution of the derivatized ligand or binder which partitions onto the surface of the forming droplets. The ligand or binder also acts as the emulsifying agent (surfactant) and the adsorbed layer prevents re-coalescence.

The degree of derivatization (substitution) required to provide secure attachment to the surface of the droplets is expected to vary significantly depending upon the nature of the perfluoro anchor group, the spatial arrangement of the anchor groups on the ligand, the size and nature of the ligand, and the eventual use of the liquid support. In general, the higher the degree of substitution the stronger the attachment. This, however, can be limited by steric considerations as well as the need to retain the biological activity of the ligand or binder. It has been found that placing anchor groups on approximately 20% of the available amino groups on a typical protein is preferred. When 20% of the amino groups of glucose oxidase and urease were labeled with perfluorooctyl imidazolide, these enzymes were found to retain substantially all of their native activity. Also, when washed with buffers, the enzymes resisted being washed off the surface of perfluorodecalin droplets.

A third method for preparing liquid supports is a variation of the partition method. In this approach, a reagent comprised of a highly or perfluoro-substituted moiety and a charged organic moiety is utilized. The highly or perfluoro-substituted portion acts as a hydrophobic moiety while the charged organic portion acts as a hydrophile, constituting a charged (ionic) surfactant. This water soluble or water miscible surfactant can be mixed with, for example, an LPF. The result is the secure attachment of the charged organic molecule (moiety) to the surface of the carrier droplets through the fluoro-substituted portion. In the laboratory, mixing can be carried out in a separatory funnel or flask; small quantities of liquid supports can be prepared by agitation with a vortex mixer. In general, after the formation of the liquid ion-exchange support, the reaction mixture can be washed with water or an aqueous buffer solution to remove excess fluoro-surfactant. The incorporated surfactant imparts stability to the emulsion while the charged portion, the ligand, imparts selectivity when the supports are used in separation and extraction procedures.

Charged organic molecules having fluoro-substituted portions include a class of surfactants available under the name of Zonyl* fluorosurfactants (a registered trademark of E. I. du Pont de Nemours and Company). These include Zonyl* FSP, FSE phosphate salts, $[F(CF_2CF_2)_{3-8}CH_2CH_2O]_{1,2}P(O)(O^-NH_4^+)_{2,1}$; Zonyl* FSC sulfate salts, $F(CF_2CF_2)_{3-8}CH_2CH_2SCH_2CH_2N^+(CH_3)_3 {}^-OSO_2OCH_3$; etc.

While the approaches described here provide good general procedures for attaching ligands or binders to the surface of the carriers, specific procedures for specific ligands or binders may need to be utilized. One such procedure would involve specific substitution of the Fc portion of an IgG class antibody with a highly fluorinated reagent allowing the attachment of the antibody to the surface of the LPF in a specific orientation. This would allow attachment of the antibody with its specific binding portions, the F(ab) binding sites, oriented into the aqueous portion of the emulsion. Such orientation is expected to provide more efficient use of the antibody and greater capture efficiency. It might also minimize nonspecific binding interferences by rheumatoid factors which might be present in the mixture by making the Fc portion of the antibody inaccessible to the aqueous phase.

While both of the above-described methods can be utilized in the instant invention, the partition method has some advantages over the direct method. These advantages include providing for preparation of individual components of the liquid affinity support permitting more rigorous quality control; promoting optimal use of expensive or scarce ligands or binders; creating a single ligand layer minimizing steric blockage of binding sites on the support; and providing multiple attachment sites on each ligand or binder promoting stronger attachment to the surface of the droplet.

The two-dimensional mobility of the ligand or binder inherent in the liquid affinity support may offer a further advantage, particularly with large macromolecules such as DNA, by allowing a zippering effect to occur. By zippering effect is meant the successive binding of various binding sites of the target molecule to mobile binding sites on the droplet surface. Such binding to each successive site of the carrier promotes alignment of the DNA with and attachment to the next binding site of the carrier. This is expected to provide secure, shear resistant capture of large and potentially fragile macromolecules. This zippering effect would not be possible with solid affinity supports.

Another advantage of liquid supports over conventional solid supports is the ability to sterilize the reagents used to form the support as well as to re-sterilize contaminated supports. The latter is not possible with solid supports. The partition method of attaching ligands or binders to the carrier is particularly amenable to re-sterilization. The perfluoro-derivatized ligand or binder can be recovered from the support using perfluorosurfactants and sterilized by ultrafiltration prior to reattachment.

The LPF's can also be sterilized by ultrafiltration or autoclaving. The support can then be reformed using the same components or fresh LPF could be substituted. This allows recovery and reuse of valuable ligand or binder. Certain supports can also be sterilized without separation of the components if the ligand or binder can retain biological activity under appropriate sterilization conditions. These considerations are particularly important to applications such as extra-corporeal blood processing or preparation of therapeutics for use in humans.

The use of the liquid affinity supports described above can be quite different from the use of conventional solid affinity supports. Liquid affinity supports offer a choice of separation modes. While solid supports are generally limited to co-current operation, liquid supports can operate in the countercurrent or in interconnected multiple batch modes. This flexibility allows the development of separation processes that are governed by the needs and contraints of the overall system rather than the need to use a particular separation method. The separated material can be recovered from the liquid affinity support through the use of dissociation agents.

In chromatographic applications, solid affinity supports usually require the use of filtered samples to prevent debris from occluding the column causing high back pressures, decreased fluid flow and generally less efficient operation. Liquid affinity supports, by their inherent deformability, resist occlusion. The inherent properties of deformability, flexibility and instant shape recovery further allow these supports to be readily transported through tubes without concern for blockage or physical attrition of the support which occur with solid supports. Even emulsions containing high concentrations of a liquid affinity support can be transported with ease.

The ability to be transported conveniently through tubes provides for ready automation of the separation process. Only standard pumps and valves are required and, in many circumstances, even solenoid valves can be avoided as a high concentration emulsion can effectively act as a valve. At a restricted orifice, the dense LPF-based slurry can resist passage through the orifice and prevent passage of the aqueous stream while allowing controlled passage of the emulsion. The flow of emulsion can be readily controlled by the dimension of the orifice and the relative fluidic pressures across this constriction.

Use of liquid affinity supports in the batch mode can also offer advantages over solid affinity supports: the separation from the aqueous phase is rapid and simple because of the high density of the support; washing of the support is simple and efficient because the support is non-porous, and the difficulties of porous supports or the fragility of extremely small particles are avoided while taking advantage of the high surface area of the support.

The bioaffinity separation method of this invention permits the utilization of countercurrent affinity separation not practicable with standard solid phase affinity supports because the latter cannot be transported reproducibly and consistently. Such separations offer the maximum capture efficiency because the leading front of the sample stream which is most depleted in the target ligand or binder is constantly exposed to fresh affinity support which has the maximal ability to capture the remaining target molecules. This can be used to great advantage to collect a dilute product from a process stream, particularly when used in a continuous process. Another advantageous use of these separations is in depleting a sample stream of deleterious substances such as waste products as has to be done in extra-corporeal plasma depletion.

The method of this invention can also be utilized in the so-called mix and sediment process. Here, the sample stream and liquid support are brought together in a mixing area which allows the target substance to be captured by the support. The resulting emulsion is then fed into a sedimentation tank where the dense affinity support settles and is drained for eventual recovery of the target substance and regeneration of the support. This mix and sediment process offers a simple approach to continuous affinity separation.

One particular analytical application of the liquid affinity supports of this invention is their use to capture DNA from solution. The partition method was used to form a liquid affinity support with histone proteins attached to the surface of the droplets. Histones are highly positively charged proteins which interact with DNA in the cell to package the DNA into a compact form. Surprisingly, it has been found that a liquid affinity support with modified calf thymus histones on the surface of perfluoro-2-butyltetrahydrofuran or other carriers can capture DNA from aqueous solution. The captured DNA-support complex can be concentrated by evaporation to afford a histone-DNA complex which is permitted to attach to a suitable membrane. Again, surprisingly, this form of the DNA was found suitable for hybridization with an appropriate probe. This approach is superior to the current liquid-liquid extraction or column elution methods both of which require concentration of the DNA after isolation from solution before it can be applied to the hybridization membrane. While histones were used in the described process other ligands, such as polylysine, anti-DNA antibodies or specific oligonucleotide sequences which would capture only complementary base sequences, can also be utilized.

Another analytical application which illustrates the advantages of the use of liquid affinity supports, is the immunoassay. One such assay is a qualitative enzyme linked immunosorbent assay (ELISA) in which color can be visually detected on the surface of filter paper, porous membrane, plastic paddle or other solid surfaces. This assay can be readily adapted to quantitative assays and to the use of other detectable signals besides color. In the traditional format of ELISA, the use of porous supports permits the colored product of the immunoassay to be trapped inside the pores diminishing its contribution to the detectable signal. Also, the colored product often diffuses into solution further diminishing the detectable signal limiting the apparent sensitivity of the assay. The apparent sensitivity of these assays can be improved by using liquid affinity supports of this invention and evaporating the support at appropriate stages of the assay. This could be after the analyte has been captured, analogous to the system described for the DNA assay above, or just before addition of the enzyme substrate to be converted into colored product.

An alternative to evaporating the liquid support is the release of the bound target substance from the ligand or binder. In the case of capturing DNA using modified calf histones, such release can be accomplished by adjusting the salt concentration of the buffers used to wash the support. In the case of an antigen capture on an antibody coated support, this might be done utilizing a high pH buffer, mild chaotropic agent or fluorosurfactants.

The liquid ion-exchange supports of this invention have utility similar to that described above for the liquid affinity supports but operate on the principles of ion-exchange.

The following examples further illustrate the invention.

EXAMPLE 1

Preparation of a Liquid Affinity Support—Direct Method

Fluorescently labeled bovine serum albumin (FITC-BSA) was prepared by adding 25 mg of fluorescein isothiocyanate (FITC) to 500 mg of bovine serum albumin (BSA) dissolved in 25 mL of 0.2M carbonate-bicarbonate buffer, pH 9.25. The reaction mixture was stirred for 30 minutes at room temperature and applied to a 25×2.2 cm column of Bio-Gel* P-6 (Bio-Rad Laboratories, Richmond, Calif.) equilibrated with 0.9% sodium chloride (normal saline). The FITC-BSA was eluted in the exclusion volume of the column, free of unreacted FITC. Spectroscopic analysis of the FITC-BSA showed that the degree of conjugation was 8.65 moles of FITC per mole of BSA.

Solutions of (perfluorooctyl) acetyl chloride, 1H,1H-perfluorodecanoyl chloride (Riedel-De-Haenag, Seelze-Hannover, West Germany) in perfluorodecalin (Flutec PP5, Medical Grade, ISC Chemicals Ltd., Avonmouth, UK) were prepared as follows. A concentrated stock solution was prepared by adding 2 mL of the acid chloride to 1 mL of perfluorodecalin. Working solutions of 0, 1, 5, 10, 20 and 40 mg of the acid chloride/mL of perfluorodecalin were prepared by adding 0, 0.25, 1.25, 2.5, 5 and 10 mL of the stock solution to 1 mL of perfluorodecalin. A density of 2 g/mL was assumed for the acid chloride when calculating the volumes required.

Emulsions of the liquid affinity support were prepared by dropwise addition of 0.1 mL of each of the working solutions prepared above into 1.0 mL of a vortexing solution of 1 mg/mL FITC-BSA in normal saline. After vortexing for 10–15 seconds, the emulsions were gently mixed for about 30 minutes on an oscillating mixer and washed by sedimentation with 1 mL of normal saline solution to remove unbound FITC-BSA. The washing was repeated twice with 1 mL each of normal saline solution.

The emulsions were examined under a fluorescence microscope for the presence of fluorescence associated with the surface of the perfluorodecalin droplets. The amount of fluorescence was greater with the higher concentrations of acid chloride used. At the 20 and 40 mg/mL concentrations of the acid chloride, some distortion of the droplets was evident. When the control working solution, that is, perfluorodecalin without acid chloride, was used, only faint fluorescence was observed. This demonstrated that there was only minimal nonspecific adsorption to the surface of the droplets and, most importantly, that no liquid affinity support was obtained when the methods of this invention for preparing these supports were not employed.

EXAMPLE 2

Preparation of Liquid Affinity Supports—Direct Method

FITC-BSA was prepared as described in Example 1. In a series of experiments, substituting different liquid perfluorocarbons for perfluorodecalin and different reactive compounds for (perfluorooctyl) acetyl chloride in the procedure of Example 1, nine additional supports were prepared. The liquid perfluorocarbons were perfluorotributylamine, perfluoro(tetradecahydrophanthralene) and perfluoro-2-butyltetrahydrofuran (all from SCM Chemicals, Gainesville, Fla.). The reactive compounds were perfluorooctanoyl chloride, perfluorooctanoic anhydride, and perfluorobenzoyl chloride (SCM Chemicals, Gainesville, Fla.).

Emulsions prepared from all combinations of these components yielded bright fluorescent layers when observed under fluorescence microscope. Control experiments in which the reactive compounds were not included, showed only faint fluorescence. This demonstrated that a variety of liquid perfluorocarbons and a variety of reactive perfluorinated compounds could be used to attach a ligand to a carrier by the direct method.

When perfluorosuccinyl chloride, a difunctional acid chloride, was used as the reactive compound, no emulsions could be obtained; rather crosslinked, gel-like materials resulted.

EXAMPLE 3

Antibody Capture by Liquid Affinity Support

A stock solution was prepared by adding 2.0 mL of perfluorooctanoyl chloride to 1 mL of perfluorotributylamine. A working solution was prepared by diluting 10 mL of the stock solution with 1 mL of perfluorotributylamine. 0.1 mL of this working solution was added dropwise to a vortexing solution of 1 mg/mL rabbit immunoglobulin G in normal saline. After vortexing for about 15 seconds, the emulsion was gently mixed for 30 minutes at room temperature. The emulsion was washed three times with 1 mL each of normal saline solution.

Most of the supernatant liquid was removed and 50 mL of 1.5 mg/mL FITC-labeled affinity purified goat anti-rabbit-IgG antibody was mixed with the emulsion of the liquid affinity support for 10 minutes at room temperature. The emulsion was then washed 3 times with 1 mL each of normal saline solution.

In an identical parallel experiment, normal saline wash solutions were replaced by wash solutions containing 1% BSA. Both resulting emulsions were examined under fluoroescence microscope and were found to have bright, even fluoroescent layers coating the droplets. This demonstrated that when the ligand attached to a carrier was rabbit IgG it was still immunochemically recognizable by an appropriate antibody. Since no difference was noted between the samples washed with or without BSA in the wash solution, there appeared to have been little or no nonspecific capture of the FITC-labeled antibody.

EXAMPLE 4

Preparation and Use of a Liquid Affinity Support—Partition Method

A. (Perfluorooctyl) propanoyl imidazolide, 1H,1H,2H,2H-perfluoroundecanoic imidazolide, was prepared from perfluorooctyl propanoic acid as follows: 4.9 g of (perfluorooctyl)propanoic acid was dissolved in 15 mL of dry THF and added to a stirred solution of 1.8 g of carbonyldiimidazole in 35 mL of dry THF at room temperature. The reaction mixture was stirred for 30 minutes, during which time the product began to crystallize. The mixture was cooled in icewater and filtered in a glass-fritted filter funnel. The crystals were washed with about 50 mL of ice-cold THF and dried with a stream of dry air. The yield of (perfluorooctyl)propanoyl imidazolide was 3.8 g, 68% of the theoretical yield. The melting point was 128° C.

6.0 mL of a 1 mg/mL solution of affinity purified goat anti-human IgG (Tago, Burlingame, Calif.) in phosphate buffer, pH 8.0 was cooled in an ice bath. 0.6 mL of a 20 mg/mL solution of (perfluorooctyl)propanoyl imidazolide, prepared as above, in THF was added dropwise to the cooled solution with stirring. The reaction was allowed to proceed for 2 hours with continuous stirring. The reaction mixture was applied to a 3×26 cm column of Bio-Gel* P-6 (Bio-Rad Laboratories, Richmond, Calif.) equilibrated with phosphate buffer, pH 8.0. The perfluoroalkylated antibody was eluted in the void volume of the column and collected in about 21 mL total volume. Its concentration was determined spectroscopically (no correction for derivatization was used) and was found to be about 0.17 mg/mL. The degree of reaction was determined as follows: The reaction mixture was analyzed for remaining amino groups by standard procedures using trinitrobenzene sulfonic acid. The amount of anchor group attached to the IgG was calculated from the difference in the amount of available amino groups present between the control (no imidazolide) and the preparations containing the imidazolide. The percent of the available amines reacted was 25%.

B. 0.25 mL of perfluorodecalin was added to 5.0 mL of a 0.10 mg/mL solution of (perfluorooctyl)propanoyl substituted goat anti-human IgG, prepared as in Step (A) above, in phosphate buffer, pH 8.0, while vortexing. The mixture was vortexed for 1 minute and then washed 3 times each with 3 mL of 0.1% aqueous BSA.

The immunochemical reactivity and capacity of the thus prepared liquid affinity support having goat anti-human IgG bound to the surface of the emulsion droplets was measured as follows: 3.2 mL of a 326 mg/mL solution of FITC-IgG (FITC labeled human IgG was prepared by the procedure of Example 1 and found to have 2.56 moles of FITC per mole of IgG) in 0.1% aqueous BSA was dispensed into quartz cuvets suitable for fluorescence measurements. To the cuvet was added a small magnetic stirring bar and 50 mL of the support. The cuvet was stirred for 1 minute, allowed to sediment for 10 minutes and the fluorescence intensity of the supernatant measured in situ. This exact procedure was repeated 11 times, then repeated with the mixing time extended to 5 minutes and finally reapeated with the mixing time extended to 30 minutes. Care was taken during this process not to expose excessively the reaction mixture to light. The fluorescence intensity of the supernatant decreased steadily throughout this process indicating removal of the FITC-labeled IgG from solution by the support. This procedure was repeated with 3.2 mL each of 163, 82 and 33 mg/mL solutions of FITC-IgG. The results are summarized in the table below and indicate that the approximate capacity of 50 mL of this support for this particular FITC-IgG is 121 mg.

TABLE

| FITC-IgG ADDED (mg) | FITC-IgG BOUND TO SUPPORT (mg) |
|---|---|
| 1043 | 121 |
| 522 | 121 |
| 262 | 84 |
| 106 | 53 |

EXAMPLE 5

DNA Extraction

A liquid affinity support based on perfluorodecalin and histone was prepared using a slight modification of the method described in Example 1. A 100 mg/mL solution of perfluorobenzoyl chloride in perfluorodecalin was prepared and 0.1 mL of this solution was added to 1 mL of a vortexing 1 mg/mL solution of calf thymus histones in phosphate buffered saline to obtain the support.

A digest of the plasmid pBR322 was made according to standard procedures using the restriction enzyme Hae II. Acceptable digestion was demonstrated by end labelling with radioactive phosphorus labelled ATP using terminal deoxynucleotidyl transferase followed by electrophoresis and autoradiography to detect the fragments. 13 distinct radioactive fragments were observed indicating acceptable digestion.

20 mL of the pBR322 digest in 10 mM tris buffer, pH 8.0, was mixed with 180 mL of 10 mM tris buffer, pH 8.0, containing 1 mM EDTA. A 5-mL sample was removed to serve as a control. To extract the DNA, 50 mL of the sedimented support was added to the remainder and the mixture rocked gently for 30 minutes. After sedimentation, a 5-mL sample of the supernatant was removed and the remaining supernatant was transferred to another tube. The extraction process was repeated four more times with fresh support emulsion.

The supernatant samples were analyzed by electrophoresis on a 6% acrylamide, 7M urea gel using standard procedures. The gel was dried and autoradiographed on Kodak XAR-5 film for about 48 hours and the film developed in a commercial processor. Examination of the autoradiograph showed that a significant quantity of the labelled nucleic acids had been adsorbed by the histone coated support. The higher molecular weight species were adsorbed while the low molecular weight species remained in solution. By comparing the electrophoretic mobility of the oligonucleotides to that of known molecular weight standards, it was estimated that oligonucleotides containing greater than 21 pairs were extracted preferentially from the mixture.

EXAMPLE 6

DNA Extraction and Hybridization

A 20 mg/mL solution of digested pBR322 prepared as in Example 5 was prepared by serial dilution of a 20 mg/mL solution in 10 mM Tris buffer, pH 8.0, containing 1 mM EDTA. 100 mL of this solution was added to 100 mL of 25 mM phosphate buffer containing 0.9% sodium chloride, 0.1% BSA, pH 7.8, in a test tube. To this was added 50 mL of a liquid affinity support based on perfluorodecalin and histone prepared as in Example 5. The tubes were capped and rocked gently for 60 minutes at room temperature. After sedimentation, the supernatant was discarded and the resulting support-DNA complex was washed with 0.5 mL of 25 mM phosphate buffer containing 0.9% sodium chloride, pH 7.8. The complex was transferred to a known position on GeneScreen+T hybridization membrane retained in a Hybri-slot apparatus (Bethesda Research Laboratories, Inc., Bethesda, Md.) in several consecutive 10-20 mL portions. The liquid perfluorocarbon carrier was allowed to evaporate between additions. A 100-mL sample of the original solution of the digest was dispensed onto other portions of the membrane. The air-dried membrane was further treated to denature, neutralize and prehybridize the nucleic acids bound to the membrane.

The membrane was hybridized with an excess of labelled pBR322 at 65° C. overnight. (Undigested pBR322 was labelled with $^{32}$phosporous using a standard nick translation system.) The membrane was washed, dried, and the dried membrane was exposed to Kodak XAR-5 film overnight. The film was developed in a commercial processor.

This complete procedure was repeated with 2 mg/mL, 200 ng/mL, 20 ng/mL, 2 ng/mL and 200 pg/mL, respectively, concentrations of the original pBR322 digest. The table below summarizes the results of the visual inspection of the autoradiograph of all samples.

TABLE

| pBR322 DIGEST CONCENTRATION | UNPROCESSED DIGEST | SUPPORT-DNA COMPLEX |
|---|---|---|
| 20 mg/mL | strong | strong |
| 2 mg/mL | strong | strong |
| 200 ng/mL | strong | strong |
| 20 ng/mL | strong | strong |
| 2 ng/mL | distinct | strong |
| 200 pg/mL | very faint | distinct |

These results indicate that DNA captured by binding to a liquid affinity support of this invention is still capable of being hybridized and that the sample can be concentrated by this procedure. This latter point is demonstrated especially by the two low concentration samples.

EXAMPLE 7

DNA Extraction and Recovery

A 10 mg/mL solution of Strain B E. coli DNA (Sigma Chemical Co., St. Louis, Mo.) was prepared by dissolving 10 mg in 1 mL of a buffer containing 20 mM tris, 10 mM sodium chloride, 1 mM EDTA, pH 8.0, in a test tube. To this solution was added 150 mL of a liquid affinity support based on histone, prepared as in Example 5. The tube was capped and rocked gently for 60 minutes at room temperature. After sedimentation the supernatant was removed and the support-DNA complex was washed with 1 mL water three times. One mL of 3.0M sodium acetate solution was added to the complex and the tube rocked for a further 60 minutes. After sedimentation, the supernatant was transferred to another tube to which was added 2.5 mL of ethyl alcohol. The tube was centrifuged at 13,000×G for approximately 5 minutes, during which time the precipitate was sedimented.

After removal of the supernatant, the pellet was dissolved in approximately 20 mL of a 20 mM tris buffer, pH 8.0. This solution, along with samples of the original DNA and a DNA-histone complex in solution, were applied to a 0.7% agarose gel and electrophoresed by conventional methods. The gel was stained with ethidium bromide to visualize the migrated DNA. The position of the fluorescent band from the pellet, compared to that of the unprocessed DNA sample demonstrated that the DNA adsorbed by the liquid affinity support of this invention was displaced by the sodium acetate treatment (without displacing the DNA-histone complex from the support) and could be recovered by ethanol precipitation.

EXAMPLE 8

Antigen Capture and Recovery

A perfluoroalkylated antibody, prepared as described in Example 4(A), was analyzed and was found to be 26% substituted. A perfluorodecalin-based liquid affinity support was prepared by the method described in Example 4(B).

A solution of radioactive human IgG was prepared by adding 10 mL of $^{125}$I human immunoglobulin containing 1.5 mCi (New England Nuclear, Boston, Mass.) to 1 mL of a 1 mg/mL solution of human IgG (Jackson ImmunoResearch Labs, Avondale, Pa.) in 0.1M sodium phosphate, pH 8.0 (PB). Fifty mL of this solution was added to 1 mL of PB containing 250 mg of goat IgG followed by 50 mL of the support.

The reaction mixture was mixed by continuous rotation of the container for thirty minutes. The mixture was allowed to settle, the supernatant was discarded and the sedimented support was washed three times with 1 mL of PB and counted in a gamma counter to determine captured bound antigen (human IgG). After counting, 1 mL of 1.0M sodium carbonate/hydroxide buffer solution, pH 11.6, was added and the mixture mixed by rotation for 30 minutes. The mixture was allowed to settle, the supernatant was discarded and the sedimented support was washed three times with 1 mL of PB and counted to determine remaining antigen. The process of antigen capture and removal was repeated in a second cycle utilizing the recovered support. The results were as follows:

| CYCLE | CPM AFTER CAPTURE | AFTER REMOVAL |
|---|---|---|
| 1 | 10554 | 8330 |
| 2 | 12985 | 10081 |

These data demonstrate that the liquid affinity support of this invention is capable of capturing antigens and that such an IgG can be displaced from the support without displacing the capturing antibody.

EXAMPLE 9

Preparation and Use of a Liquid Cation Exchange Support

A cation exchange support was prepared by mixing 20 mL of perfluorodecalin, 20 mL of deionized water, and 4 mL of Zonyl* FSP, an anionic fluorosurfactant, in a 50 mL polypropylene centrifuge tube. This mixture was agitated vigorously on a vortex-mixer for 10-15 seconds, and then centrifuged at approximately 1000 rpm for 3-5 minutes. The aqueous layer was removed and 20 mL of deionized water was added to the emulsion. The emulsion was mixed on the vortex-mixer and centrifuged as described above. This washing procedure, which removes the excess fluorosurfactant, was repeated three times.

This cation exchange support emulsion was used to extract a positively charged dye from an aqueous solution. One milliliter of a methylene blue solution (8.8 mg/L) was added to one milliliter of the emulsion. The mixture was vortexed for several seconds and the emulsion was allowed to settle for several minutes. The aqueous phase was removed and the absorbance was measured spectrophotometrically at 666 nm. The absorbance of the initial dye solution was 1.617; it decreased to 0.0118 after the extraction, demonstrating the successful removal of 99% of the dye with a liquid ion-exchange support of this invention.

EXAMPLE 10

Preparation and Use of an Anion Exchange Support

An anion exchange support emulsion was prepared as described in Example 9, using the same quantities, except that Zonyl* FSC, a cationic fluorosurfactant, was substituted for Zonyl* FSP.

This emulsion was used to extract a negatively charged dye from an aqueous solution. One milliliter of a cresol red solution (12 mg/L in 0.050M $NaH_2PO_4$ solution) was added to one milliliter of the emulsion. This mixture was vortexed for several seconds and the emulsion was allowed to settle for several minutes. The aqueous phase was removed and the absorbance was measured spectrophotometrically at 434 nm. The absorbance decreased from 0.6250, for the initial dye solution, to 0.0122 after extraction, indicating that 98% of the dye had been removed.

Approximately 74% of the dye was successfully recovered from the support by washing it four times with one-milliliter portions of a solution containing 1.0M NaCl and 0.050M $NaH_2PO_4$.

EXAMPLE 11

Separation of Dyes Using a Cation Exchange Support

Two milliliters of a purple aqueous solution (pH adjusted to 8 with NaOH) containing methylene blue (approximately 9 mg/L) and cresol red (approximately 12 mg/L) was added to two milliliters of the cation exchange emulsion, which was prepared as described in Example 9. This mixture was vortexed vigorously and the emulsion was allowed to settle for several minutes. The lower perfluorocarbon phase became blue, leaving the red colored dye in the aqueous layer, demonstrating the separation of oppositely charged species by liquid ion-exchange supports of this invention.

EXAMPLE 12

Extraction of a Protein Using a Liquid Anion Exchange Support

An anion exchange support was prepared by adding 20 mL of deionized water, 20 mL of perfluorodecalin, and 50 mL of a 1:4 mixture of Zonyl* FSN, a neutral fluorosurfactant, and Zonyl* FSC, a cationic fluorosurfactant, to a 125-mL separatory funnel. Zonyl* FSN was used to stabilize the emulsion and to reduce nonspecific adsorption of proteins. The mixture was shaken gently and allowed to settle for 5 minutes. Three layers were formed in the separatory funnel. The bottom layer, containing the liquid support, was removed and retained and the middle (aqueous) phase was discarded. To the remaining foam (top layer), deionized water was added and the resulting perfluorocarbon support emulsion was combined with the initially retained support. This was washed twice with equal volumes of water.

Two milliliters of a 10 mM, pH 6.0 phosphate buffer containing 50 mg/mL of fluorescein-labeled human serum albumin (FITC-HSA) was added to two milliliters of the anion exchange support emulsion. The mixture was vortexed vigorously and the emulsion was allowed to settle for several minutes. The aqueous layer was removed and the emulsion was washed four times with 2-mL portions of the buffer solution. A small portion of the emulsion was removed and examined under a fluoroescence microscope. Fluorescence was observed on the surface of the droplets, demonstrating the presence of the labeled HSA. No fluorescence was observed on the surface of the droplets when the experiment was repeated with a neutral emulsion prepared with Zonyl* FSN in the absence of Zonyl* FSC.

The experiment described above was repeated and any fluorescence remaining in the aqueous phase after the first extraction with the ion-exchange support was measured with a fluorometer. This measurement indicated that 96% of the protein had been removed from the aqueous phase. 75% of the FITC-HSA could be recovered successfully by extracting four times with two milliliter portions of a 0.25M $NaH_2PO_4$ solution. At these same conditions, only small amounts (<25%) of fluorescein labeled IgG (FITC-IgG) was extracted, demonstrating the feasibility of protein separation using liquid ion-exchange supports of this invention.

EXAMPLE 13

Capture of IgG

A modified Protein A was perfluoroalkylated by dissolving 25 mg of a recombinant modified Protein A (expressed in E. Coli and lacking C-terminal domain, obtained from Porton Products Ltd. U.K.) in 25 mL of 0.10M phosphate buffer, pH 8.5 (PB). Next, 0.5 mL of a 0.5% (v/v) solution of perfluorooctylpropyl isocyanate in tetrahydrofuran (THF) was added. After the addition of an additional 4.5 mL of pure THF, the reaction mixture was mixed gently and allowed to react for 2 hours. The reaction mixture was then centrifuged at 3,000 rpm for 5 min. to remove any denatured protein or other insoluble reaction by-products.

A liquid affinity support was prepared by adding 100 mL of perfluorodecalin, 100 mL of 0.10M phosphate buffer, pH 8.5, and 1.0 mL of perfluoroalkylated modified Protein A (prepared above) to each of four 1.5-mL micro centrifuge tubes. The tubes were shaken and then vortexed. Next, 28.9 mL of 1.0, 0.1, 0.001 and 0% (w/v) solutions, respectively, of a blocking agent in water were added to each of the tubes and the tubes were again shaken and vortexed. The emulsion formed exhibited acceptable stability, except when no blocking agent was utilized.

The blocking agent was prepared by first preparing $F(CF_2)_6CH_2CH_2OH$. This alcohol, in turn, was prepared by reacting $F(CF_2)_6CH_2CH_2I$ with sulfuric acid followed by hydrolysis to give the alcohol. The iodide was obtained by distillation of Zonyl* TelB fluorochemical intermediate (a registered trademark of E. I. du Pont de Nemours and Company). The blocking agent was prepared by reacting the alcohol (prepared above) with ethylene oxide in the presence of a mixed catalyst (NaBH₄ and NaH) at 110° C. The ethylene oxide was bubbled through the reaction mixture until the equivalent of an average of 14 units of ethylene oxide had been added to the alcohol. The reaction mixture was then neutralized with acetic acid. The blocking agent so produced has the average structure:

$$F(CF_2)_6(CH_2)_2-O-(CH_2CH_2O)_{14}H$$

In order to test the ability of the modified Protein A-LPF affinity support to capture IgG (for subsequent removal of the purified IgG), several aliquots, ranging from 20-50 mL, of a 1.0 mg/mL solution of FITC-IgG (human) was added to the tube and the tube was shaken and vortexed. The supernatant was removed and 100 mL of PB was added to wash the support; the tube was shaken and vortexed, and the supernatant removed. This washing step was repeated twice with 50 mL of PB. The affinity support was then viewed under a fluorescence microscope. In all cases, fluorescence was observed on the surface of the droplets (support) indicating that the modified Protein A on the surface of the support was active and able to bind IgG. When treated with a glycine-HCl buffer (pH 3), the IgG was removed into the aqueous portion as shown by total protein assay and fluorescence measurements.

We claim:

1. A liquid affinity support containing an attached ligand or binder for the ligand consisting essentially of:

(a) a chemically inert, water immiscible liquid perfluorocarbon carrier having specific gravity greater than that of water and further having low nonspecific binding to a ligand or binder for the ligand; and (b) a perfluorocarbon-substituted ligand or binder for the ligand securely but reversibly attached to the surface of said carrier through a highly fluorinated isocyanate anchor group.

2. The liquid affinity support of claim 1, wherein said ligand is a nucleic acid.

3. The liquid support of claim 1 wherein the highly fluorinated isocyanate anchor group is a compound of the formula:

$$R_F-CH_2CH_2CH_2NCO$$

wherein $R_F$ is a linear, branched or cyclic perfluorinated radical containing 1-20 carbon atoms.

4. The liquid support of claim 3 wherein $R_F$ is $F(CH_2)_8$.

5. The support of claim 1, wherein said ligand is an antigen.

6. The support of claim 1, wherein said ligand is a hapten.

7. The liquid affinity support of claim 1, wherein said ligand is an enzyme substrate.

8. The liquid affinity support of claim 1, wherein said ligand is an enzyme inhibitor.

* * * * *